(12) United States Patent
Yamakage et al.

(10) Patent No.: US 8,085,404 B2
(45) Date of Patent: Dec. 27, 2011

(54) GAS ANALYZER AND GAS ANALYZING METHOD

(75) Inventors: Masahiro Yamakage, Anjo (JP); Katsutoshi Goto, Okazaki (JP); Kenji Muta, Yokohama (JP); Yoshihiro Deguchi, Yokohama (JP); Shinichiro Asami, Kobe (JP); Satoshi Fukada, Kobe (JP)

(73) Assignees: Toyota Jidosha Kabushiki Kaisha, Toyota (JP); Mitsubishi Heavy Industries, Ltd., Tokyo (JP)

( * ) Notice: Subject to any disclaimer, the term of this patent is extended or adjusted under 35 U.S.C. 154(b) by 315 days.

(21) Appl. No.: 12/309,584

(22) PCT Filed: Aug. 23, 2007

(86) PCT No.: PCT/JP2007/066817
§ 371 (c)(1),
(2), (4) Date: Jan. 23, 2009

(87) PCT Pub. No.: WO2008/023833
PCT Pub. Date: Feb. 28, 2008

(65) Prior Publication Data
US 2009/0323068 A1    Dec. 31, 2009

(30) Foreign Application Priority Data

Aug. 23, 2006  (JP) ................ 2006-226731

(51) Int. Cl.
*G01N 21/00* (2006.01)
(52) U.S. Cl. ...... 356/437; 250/428; 250/343; 250/338.5; 356/433; 356/440
(58) Field of Classification Search .......... 356/433–440; 250/428, 432 R, 343, 345, 338.5
See application file for complete search history.

(56) References Cited

U.S. PATENT DOCUMENTS

| 3,207,026 A | 9/1965 | Churchill et al. |
| 3,958,122 A | 5/1976 | Jowett et al. |
| 4,432,649 A | 2/1984 | Krause |

(Continued)

FOREIGN PATENT DOCUMENTS

DE   199 04 691 A1   9/2000

(Continued)

OTHER PUBLICATIONS

Sep. 16, 2010 Office Action issued in U.S. Appl. No. 12/224,793.

(Continued)

*Primary Examiner* — Michael A Lyons
*Assistant Examiner* — Iyabo S Alli
(74) *Attorney, Agent, or Firm* — Oliff & Berridge, PLC (57) ABSTRACT

A gas analyzer capable of measuring a concentration of a gas component in gas at sensor units provided at a plurality of positions in real time by decreasing the number of signals input from the sensor units to an analyzer so as to reduce a data amount input to the analyzer and a gas analyzing method. The gas analyzing method includes the steps of: demultiplexing laser light by a demultiplexer into measurement laser light and reference laser light; letting the measurement laser light pass through gas to be received by a photoreceiver; finding an absorption spectrum absorbed by a gas component in the gas based on a light intensity of the received measurement laser light and of the reference laser light; and analyzing the absorption spectrum to measure a concentration of the gas component.

15 Claims, 7 Drawing Sheets

U.S. PATENT DOCUMENTS

| | | | |
|---|---|---|---|
| 5,060,505 | A | 10/1991 | Tury et al. |
| 5,096,834 | A | 3/1992 | Saito |
| 5,173,749 | A | 12/1992 | Tell et al. |
| 5,185,645 | A | 2/1993 | Sartorius et al. |
| 5,275,553 | A | 1/1994 | Frish et al. |
| 5,381,010 | A | 1/1995 | Gordon |
| 5,572,031 | A | 11/1996 | Cooper et al. |
| 5,585,636 | A * | 12/1996 | Dollansky ............... 356/437 |
| 6,107,631 | A | 8/2000 | He |
| 6,150,661 | A | 11/2000 | McCaul et al. |
| 6,154,284 | A | 11/2000 | McAndrew et al. |
| 6,496,258 | B1 | 12/2002 | Leipertz et al. |
| 6,542,831 | B1 | 4/2003 | Moosmuller et al. |
| 6,674,528 | B2 | 1/2004 | Adachi et al. |
| 6,809,825 | B2 | 10/2004 | Kaufmann |
| 7,041,153 | B2 | 5/2006 | Totoki |
| 7,365,352 | B2 | 4/2008 | Muta et al. |
| 7,650,780 | B2 | 1/2010 | Hall |
| 2003/0160174 | A1 | 8/2003 | Grant et al. |
| 2004/0064243 | A1 | 4/2004 | Nakamura |
| 2004/0237505 | A1 | 12/2004 | Leipertz |
| 2006/0256330 | A1 | 11/2006 | Leipertz |
| 2009/0039284 | A1 * | 2/2009 | Goto et al. ............... 250/432 R |
| 2009/0095918 | A1 | 4/2009 | Iwase et al. |
| 2009/0164138 | A1 | 6/2009 | Goto et al. |
| 2009/0229250 | A1 | 9/2009 | Yamakage et al. |

FOREIGN PATENT DOCUMENTS

| | | |
|---|---|---|
| DE | 101 50 970 A1 | 4/2003 |
| DE | 103 09 604 A1 | 9/2004 |
| EP | 0 768 521 A1 | 4/1997 |
| EP | 1 398 617 A1 | 3/2004 |
| JP | A-55-83839 | 6/1980 |
| JP | B2-64-1740 | 1/1989 |
| JP | A-3-25352 | 2/1991 |
| JP | A-3-31726 | 2/1991 |
| JP | A-3-107744 | 5/1991 |
| JP | A-3-505131 | 11/1991 |
| JP | A-4-16749 | 1/1992 |
| JP | A-4-27846 | 1/1992 |
| JP | B2-5-77023 | 10/1993 |
| JP | A-6-148072 | 5/1994 |
| JP | A-8-54339 | 2/1996 |
| JP | A-8-278179 | 10/1996 |
| JP | A-8-338805 | 12/1996 |
| JP | U-63-107845 | 7/1998 |
| JP | B2-2837442 | 12/1998 |
| JP | A-11-83734 | 3/1999 |
| JP | A-11-325427 | 11/1999 |
| JP | A-2000-74830 | 3/2000 |
| JP | A-2000-206041 | 7/2000 |
| JP | A-2000-510950 | 8/2000 |
| JP | A-2000-283915 | 10/2000 |
| JP | A-2000-314342 | 11/2000 |
| JP | A-2001-74653 | 3/2001 |
| JP | A-2001-124674 | 5/2001 |
| JP | A-2001-174410 | 6/2001 |
| JP | A-2002-48711 | 2/2002 |
| JP | A-2002-506222 | 2/2002 |
| JP | A-2002-131198 | 5/2002 |
| JP | A-2003-114192 | 4/2003 |
| JP | A-2003-139701 | 5/2003 |
| JP | A-2003-215036 | 7/2003 |
| JP | A-2003-344244 | 12/2003 |
| JP | A-2004-55183 | 2/2004 |
| JP | A-2004-117259 | 4/2004 |
| JP | A-2004-264146 | 9/2004 |
| JP | A-2004-317148 | 11/2004 |
| JP | A-2005-23249 | 1/2005 |
| JP | A-2005-24251 | 1/2005 |
| JP | A-2006-58009 | 3/2006 |
| JP | A-2006-184180 | 7/2006 |
| WO | WO 97/43609 | 11/1997 |
| WO | WO 99/46578 | 9/1999 |
| WO | WO 02/095376 A2 | 11/2002 |
| WO | WO 2005/077001 A2 | 8/2005 |
| WO | WO 2005/077001 A3 | 8/2005 |
| WO | WO 2005/111585 A2 | 11/2005 |
| WO | WO 2005/111585 A3 | 11/2005 |
| WO | WO 2006/118347 A1 | 11/2006 |
| WO | WO 2007/069786 A1 | 6/2007 |

OTHER PUBLICATIONS

Deguchi et al., "Development of direct and high response exhaust gas measurement (2); The techniques and the performance evaluation of the measurement equipment," *Preprints of Meeting on Automotive Engineers*, May 23, 2007, No. 12-07, pp. 25-28.

Abe et al., "Advanced Combustion Control System by Real-time Measurement of CO, $O_2$ Concentration in Refuse Incineration Plant," *Mitsubishi Heavy Engineering Report*, vol. 38, No. 1, 2001, pp. 20-23 and 62.

Jan. 31, 2011 Notice of Allowance in U.S. Appl. No. 12/224,793.

Office Action issued by the U.S. Patent and Trademark Office in U.S. Appl. No. 11/918,650 on Mar. 5, 2010.

Supplementary European Search Report issued in European Patent Application No. 06732512.6 mailed Mar. 17, 2010.

Supplementary European Search Report issued in European Patent Application No. 07744631, dated Jan. 30, 2009.

International Search Report issued in Application No. PCT/JP2007/061245 mailed Sep. 4, 2007 (with Translation).

Office Action issued in U.S. Appl. No. 12/159,042 on Apr. 16, 2010.

International Search Report issued in Application No. PCT/JP2006/325566 mailed Jan. 23, 2007.

International Search Report issued in Application No. PCT/JP2006/309360 mailed May 30, 2006 (with Translation).

Yamakage ct al., "Development of direct and high response exhaust gas measurement (I)," *Society of Automotive Engineers of Japan, Inc.*, Publication No. 20075153, No. 12-07, pp. 21-24, 2007 (with Translation).

U.S. Appl. No. 12/224,793 filed Sep. 5, 2008 in the name of Tomoyasu Iwase et al.

U.S. Appl. No. 12/083,521 filed Apr. 11, 2008 in the name of Katsutoshi Goto et al.

U.S. Appl. No. 11/918,650 filed Nov. 17, 2007 in the name of Katsutoshi Goto et al.

International Search Report issued in Application No. PCT/JP2007/066817 mailed Nov. 27, 2007.

Supplementary European Search Report issued in European Patent Application No. 06843037 mailed on May 11, 2009.

Yamakage et al., "Development of Direct and Fast Response Gas Measurement," Publication No. 2008-01-0758, 2008.

Yamakage et al., "Development of Direct and High Response Gas Measurement," Publication No. 20070351, 2007 (with Abstract).

Davidy et al., "Development of Inverse Radiative Method for Measuring Gaseous and Particles Concentrations in the Exhaust Plumes by Using Remote Sensing Method," $41^{th}$ *AIAA/ASME/SAE/ASEE Joint Propulsion Conference & Exhibit*, AIAA 2005-3577, pp. 1-21, 2005.

Kubota et al., "Kogaku Gijutsu Handbook," pp. 1112-1117, Apr. 1997 (with Translation).

U.S. Appl. No. 12/159,042, filed Jun. 24, 2008 in the name of Masahiro Yamakage et al.

Aug. 22, 2011 Supplemental Search Report issued in European Application No. 07806294.0.

* cited by examiner

GAS ANALYZER AND GAS ANALYZING METHOD

TECHNICAL FIELD

The present invention relates to a gas analyzer, and more particularly relates to a gas analyzer and a gas analyzing method, capable of determining a concentration or the like of a gas component contained in gas flowing through a gas flowing path such as an exhaust path of an engine in real time.

BACKGROUND ART

Conventionally, a vehicle-mounted HC measurement device described in JP Published Patent Application No. 2004-117259 A (Patent Document 1) is available as an exhaust gas analyzer for car or the like. This vehicle-mounted HC measurement device is adapted to allow a NDIR (non-dispersive infrared spectroscopy) gas analyzer, an exhaust gas flowmeter and an arithmetic operation circuit to be installed in a vehicle, the NDIR for continuously measuring a HC (hydrocarbon) concentration in exhaust gas flowing through an exhaust tube connected with an engine, the exhaust gas flowmeter continuously measuring a flow rate of the exhaust gas flowing through the exhaust tube, and the arithmetic operation circuit performing arithmetic operation of an output from the NDIR gas analyzer and an output from the exhaust gas flowmeter to continuously calculate a THC (total hydrocarbon) amount in the exhaust gas.

Although the above-stated exhaust gas analyzer described in Patent Document 1 can facilitate measuring the THC in exhaust gas of a vehicle when the vehicle is moving on a real road, it is impossible to conduct analysis of the exhaust gas in real time because the exhaust gas has to be transferred for analysis of gas components from the exhaust path of the engine to an analysis section through a pipe. Further, in order to reduce the above-described units in size, analysis is carried out only for a limited component such as HC. At the development stage of an engine or attachments to the engine such as an exhaust gas purifier, it has been desired to provide an exhaust gas analyzer facilitating the measurement of components other than hydrocarbon in exhaust gas, such as nitrogen oxides and carbon monoxide, while being capable of measuring a component of the exhaust gas or a gas concentration in real time.

Figure 7:
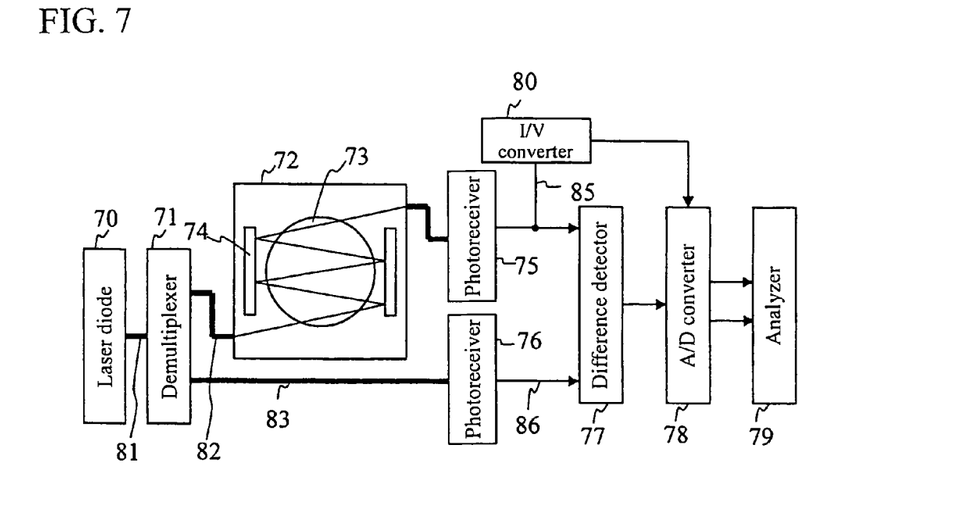
FIG. 7 is a block diagram illustrating a gas analyzer including the major configuration of a laser oscillation/photoreceiving controller and a signal analyzer that the applicant of the present invention has developed.

Then, the applicant of the present invention has developed a gas analyzer capable of facilitating the measurement of even a large number of gas components in gas such as nitrogen oxides and carbon monoxide in real time. FIG. 7 illustrates the gas analyzer.

A sensor unit 72 includes a through hole 73 formed at a center thereof, and includes reflecting mirrors 74, 74 opposed to each other to sandwich the through hole 73 therebetween. This sensor unit 72 is disposed in a gas flowing path such as an exhaust tube connected with an engine, and is configured so that gas flowing through the through hole 73 of the sensor unit 72 is emitted with laser light.

A laser diode 70 emits laser light of a wavelength band including a wavelength absorbed by a gas component to be measured, and the emitted laser light is guided to a demultiplexer 71 via an optical fiber 81 and is demultiplexed by the demultiplexer 71 into measurement laser light and reference laser light. The thus demultiplexed measurement laser light is guided to an emission unit of the sensor unit 72 via an optical fiber 82, and is applied to gas flowing in the through hole 73 through the emission unit. While the measurement laser light applied to the gas is reflected a plurality of times between the reflecting mirrors 74, 74, the laser light of a specific wavelength is absorbed by a gas component contained in the gas, so as to be received by a photoreceiver 75. The received measurement laser light is converted into an electric signal 85 by the photoreceiver 75, and the electric signal 85 is output to a difference detector 77 and an I/V converter 80. The electric signal 85 input to the I/V converter 80 is I/V converted by the I/V converter 80, and is further converted into a digital signal by an A/D converter 78, which is then input to an analyzer (computer) 79 as a measurement received-light intensity signal.

On the other hand, the reference laser light is guided to a photoreceiver 76 via an optical fiber 83, and is received by the photoreceiver 76 to be converted into an electric signal 86. The electric signal 86 is output to the difference detector 77. The difference detector 77 calculates a difference between the electric signal 85 for the measurement laser light that has passed through the gas and the electric signal 86 for the reference laser light that does not pass through the gas. The calculated differential signal is converted into a digital signal by the A/D converter 78, and is output to the analyzer (computer) 79.

Based on the differential signal input by the difference detector 77 and the electric signal 85 from the photoreceiver 75 indicating the measurement received-light intensity, the analyzer 79 finds an absorption spectrum (standardized absorption spectrum) when the measurement laser light of a predetermined intensity passes through the gas. The analyzer 79 compares the calculated absorption spectrum with a theoretical spectrum for analysis to measure a concentration of a gas component contained in the gas as well as a temperature and a pressure of the gas.

Patent Document 1: JP Published Patent Application No. 2004-117259 A

DISCLOSURE OF THE INVENTION

Problem to be Solved by the Invention

Figure 8:
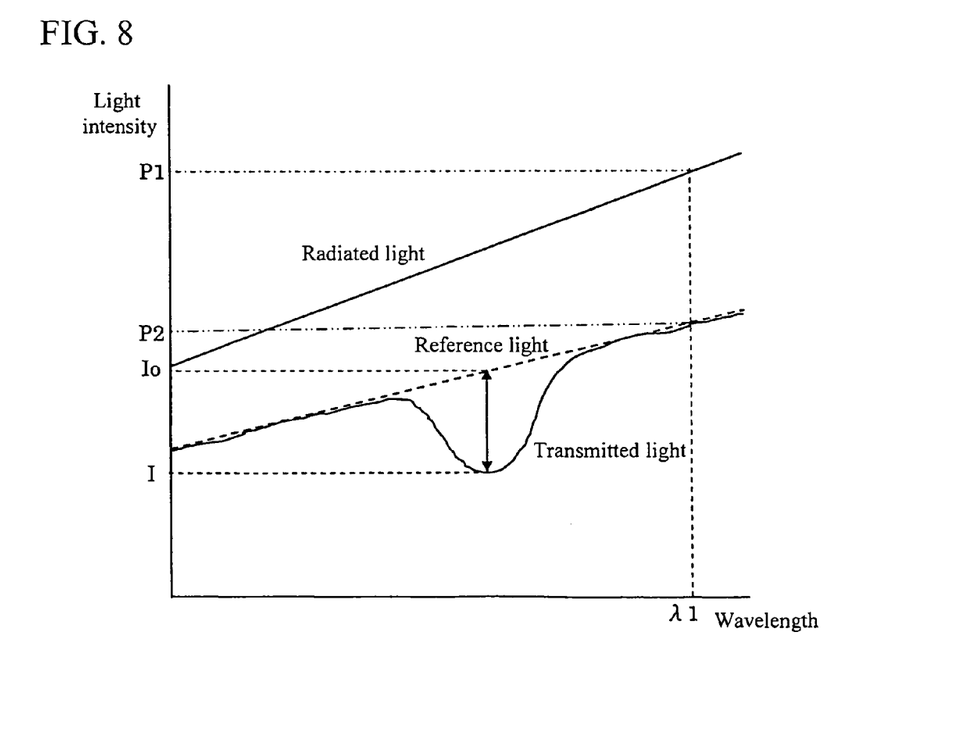
FIG. 8 explains an absorption spectrum in the present invention.

In the gas analyzer of FIG. 7, the measurement laser light applied to the exhaust gas in the sensor unit 72 as the measurement region will be attenuated due to dirt on the reflecting mirrors 74 caused by the exhaust gas or scattering by particles floating in the exhaust gas. For example, as shown in FIG. 8, the applied measurement light with light intensity P1 and wavelength λ1 will be attenuated during the passage through the exhaust gas to light intensity P2 at the time of the reception by the photoreceiver 75. Herein, the attenuation ratio of the measurement light during the passage through the exhaust gas varies and is not constant due to the degree of the dirt on the reflecting mirrors 74 or the state of the particles floating in the exhaust gas.

To cope with this, the analyzer 79 calculates a standardized absorption spectrum obtained when the measurement light of a certain light intensity passes through the exhaust gas, based on two signals of the differential signal from the difference detector 77 and the measurement received-light intensity signal from the I/V converter 80.

Thus, the signal analyzer 79 in the gas analyzer of FIG. 7 receives a large amount of digital data as an input, i.e., the two signals including the differential signal and the received-light intensity signal.

However, the capacity of a PCI bus currently employed in a signal conversion board used for a typical measurement system is about 100 MB/sec, and a gas analyzer also uses such a typical signal conversion board. Therefore, if data sampling exceeding 1 MHz is to be performed, the digital data amount input from the A/D converter 78 to the analyzer 79 will be restricted by the capacity of the PCI bus.

FIG. 7 describes the case of measuring exhaust gas at one position of the exhaust path of the vehicle. However, an exhaust path of a vehicle usually is provided with an exhaust gas purifier, and exhaust gas has to be measured before and after the exhaust gas purifier, which means that exhaust gas usually has to be measured at a plurality of positions along the exhaust path. Furthermore, since a wavelength of laser light absorbed varies depending on a gas component contained, an increase in the number of gas components to be measured will widen the wavelength range of the laser light. Thus, an increase in the number of gas components to be measured will lead to an increase in the amount of data input to the analyzer 79, thus causing a restriction on the number of positions of measurement.

In view of the above-stated problems, it is an object of the invention to provide a gas analyzer capable of measuring concentrations of a plurality types of gas components in real time even when sensor units are provided at a plurality of positions by decreasing the number of signals input from the sensor units to an analyzer so as to reduce the data amount input to the analyzer.

Means for Solving the Problem

A gas analyzing method of the present invention includes the steps of: demultiplexing laser light by a demultiplexer into measurement laser light and reference laser light; letting the measurement laser light pass through gas to be received by a photoreceiver; finding an absorption spectrum absorbed by a gas component in the gas based on a light intensity of the received measurement laser light and a light intensity of the reference laser light; and analyzing the absorption spectrum to measure a concentration of the gas component. The measurement laser light is applied to the gas through an optical attenuator, and control is conducted by the optical attenuator so that the light intensity of the measurement laser light that has passed through the gas has a predetermined relationship with the light intensity of the reference laser light.

A gas analyzer of the present invention includes: a demultiplexer that demultiplexes laser light into measurement laser light and reference laser light, the laser light being emitted from a laser light emission unit; an emission unit that radiates gas with the measurement laser light; a measurement light photoreceiver that receives the measurement laser light that has passed through the gas; and a reference light photoreceiver that receives the reference laser light. The measurement laser light is applied by the emission unit through an optical attenuator, and an attenuation ratio of the optical attenuator is controlled so that the light intensity of the measurement laser light received by the measurement light photoreceiver has a predetermined relationship with the light intensity of the reference laser received by the reference light photoreceiver.

According to the present invention, the optical attenuator is feed-back controlled so that the light intensity of the measurement laser light received by the photoreceiver has a predetermined relationship with the light intensity of the reference laser received by the photoreceiver, and therefore the measurement laser light received by the photoreceiver can be controlled so as to always have a predetermined relationship with the light intensity of the reference laser light even when the degree of dirt on the reflecting boards and the state of the particles floating in the exhaust gas change. Thus, according to the present invention, the light intensity of the measurement laser light that has passed through gas can be determined based on the light intensity of the reference laser light, and there is no need to input a signal of the light intensity of the measurement laser light to the analyzer. As a result, the data amount to be input to the analyzer can be reduced, thus enabling an increase in the measurement positions and the number of measured gas components, In a preferred embodiment of the present invention, the measurement laser light is demultiplexed by a demultiplexer into a plurality of laser light beams, and the demultiplexed plurality of measurement laser light beams are applied to the gas at different positions so as to measure a gas component concentration in the gas at a plurality of positions.

A gas analyzing method of the present invention includes the steps of: demultiplexing a plurality of laser light beams each having a different wavelength band by a demultiplexer into a measurement light beam and a reference light beam; letting the respective measurement light beams pass through optical attenuators and then multiplexing the same to be measurement laser light; letting the measurement laser light pass through gas and demultiplexing the same by a wavelength-specific demultiplexer into transmitted light for each wavelength band; multiplexing the respective reference light beams to be reference laser light and then demultiplexing the same by a wavelength-specific demultiplexer into reference light for each wavelength band; finding an absorption spectrum absorbed by a gas component in the gas based on a light intensity of the transmitted light demultiplexed by the wavelength-specific demultiplexer and a light intensity of the reference light demultiplexed by the wavelength-specific demultiplexer and analyzing the absorption spectrum to measure a concentration of the gas component. Control is conducted by the optical attenuators so that a light intensity of the transmitted light of a certain wavelength band demultiplexed by the wavelength-specific demultiplexer has a predetermined relationship with a light intensity of the reference laser light of the certain wavelength band.

A gas analyzer of the present invention includes: a plurality of laser light emission units that emit a plurality of laser light beams each having a different wavelength band; a demultiplexer that demultiplexes each laser light beam having a different wavelength band into a measurement light beam and a reference light beam; a multiplexer that multiplexes the measurement light beams each having a different wavelength band to be measurement laser light; a multiplexer that multiplexes the reference light beams each having a different wavelength band to be reference laser light; an emission unit that emites gas with the measurement laser light; a wavelength-specific demultiplexer that demultiplexes the measurement laser light that has passed through the gas into transmitted light for each wavelength band; and a wavelength-specific demultiplexer that demultiplexes the reference light into reference light for each wavelength band. The respective measurement light beams are multiplexed by the multiplexer via an optical attenuator, and an attenuation ratio of the optical attenuator is controlled so that a light intensity of the transmitted light of a certain wavelength band demultiplexed by the wavelength-specific demultiplexer has a predetermined relationship with a light intensity of the reference light of the certain wavelength band.

According to the present invention, a plurality of laser light beams each having a different wavelength band are demultiplexed by a demultiplexer into a measurement light beam and a reference light beam; the respective measurement light beams pass through optical attenuators and then are multiplexed to be measurement laser light; the measurement laser light pass through gas and is demultiplexed by a wavelength-specific demultiplexer into transmitted light for each wavelength band. Further, the respective reference light beams are multiplexed to be reference laser light, which is then demultiplexed by a wavelength-specific demultiplexer into reference light for each wavelength band. Then, an absorption spectrum absorbed by a gas component in the gas can be found based on a light intensity of the measurement laser light demultiplexed by the wavelength-specific demultiplexer and the light intensity of the reference light demultiplexed by the wavelength-specific demultiplexer, and the absorption spectrum can be analyzed to measure a concentration of the gas component. Further, an attenuation ratio of the optical attenuator is controlled so that the light intensity of the transmitted light of a certain wavelength band demultiplexed by the wavelength-specific demultiplexer has a predetermined relationship with the light intensity of the reference light of the certain wavelength band, and therefore there is no need to input a signal of the light intensity of the transmitted light demultiplexed by the wavelength-specific demultiplexer to the analyzer. Thus, the data amount transmitted to the analyzer can be reduced, and a plurality of gas components contained in the exhaust gas can be analyzed at a plurality of positions within the range of the capacity of a PCI bus in the analyzer to measure concentrations thereof, for example. Therefore, according to the present invention, concentrations of ammonia (1530 nm), carbon monoxide (1560 nm), carbon dioxide (1570 nm), methane (1680 nm), and water (1350 nm) and the like can be determined at one time.

In a preferred embodiment of the present invention, the plurality of laser light emission units that emit the plurality of laser light beams each having a different wavelength band are emitted in a time-sharing manner so that each laser light beam is emitted in a different time period. With this configuration, the data amount to the analyzer can be reduced, and analysis data for different wavelength bands are never mixed, so that the concentrations of the gas components can be determined stably.

In a preferred embodiment of the present invention, the laser light beams each having a different wavelength band are emitted from the plurality of laser light emission units, and are demultiplexed into the plurality of laser light beams by a demultiplexer, and the plurality of measurement laser light beams are applied to the gas at different positions so as to measure a gas component concentration in the gas at a plurality of positions.

The present application claims priority on Japanese Patent Application No. 2006-226731, the specification and/or the drawings of which are hereby incorporated herein by reference.

EFFECTS OF THE INVENTION

According to the present invention, gas is emitted with measurement laser light via an optical attenuator, and control is conducted by the above-stated optical attenuator so that the light intensity of the measurement laser light that has passed through the gas has a predetermined relationship with the light intensity of the reference laser light. Therefore, there is no need to input data of the light intensity of the measurement laser light that has passed through the gas to an analyzer. Thus, the data amount to be input to the analyzer can be reduced, which is for analyzing a concentration or the like of a gas component contained in the gas based on the measurement laser light that has passed through the gas and the reference laser light that does not pass through the gas. As a result, concentrations of a plurality of types of gas components contained in the gas can be analyzed for measurement at a plurality of positions in real time.

In these drawings, the respective reference numbers denote the followings:
10, 10A, 10B, 10C sensor unit
20 laser diode
22, 22A, 22B, 22C demultiplexer
23, 24A, 24B, 24C optical attenuator
25 photoreceiver (detector)
27, 27A, 27B, 27C difference detector
28, 28A, 28B, 28C A/D converter
29 analyzer
30 I/V converter
31 attenuator controller
33 NO laser diode
34 oxygen laser diode
35, 36 multiplexer
37, 38 wavelength-specific demultiplexer.
39 NO photoreceiver
40 NO laser diode
41 photoreceiver for NO reference light
42 oxygen photoreceiver
43 oxygen demultiplexer
51, 52, 53, 53A, 53B, 53C, 54 optical fiber
58 I/V converter

BEST MODE FOR CARRYING OUT THE INVENTION

Figure 1:
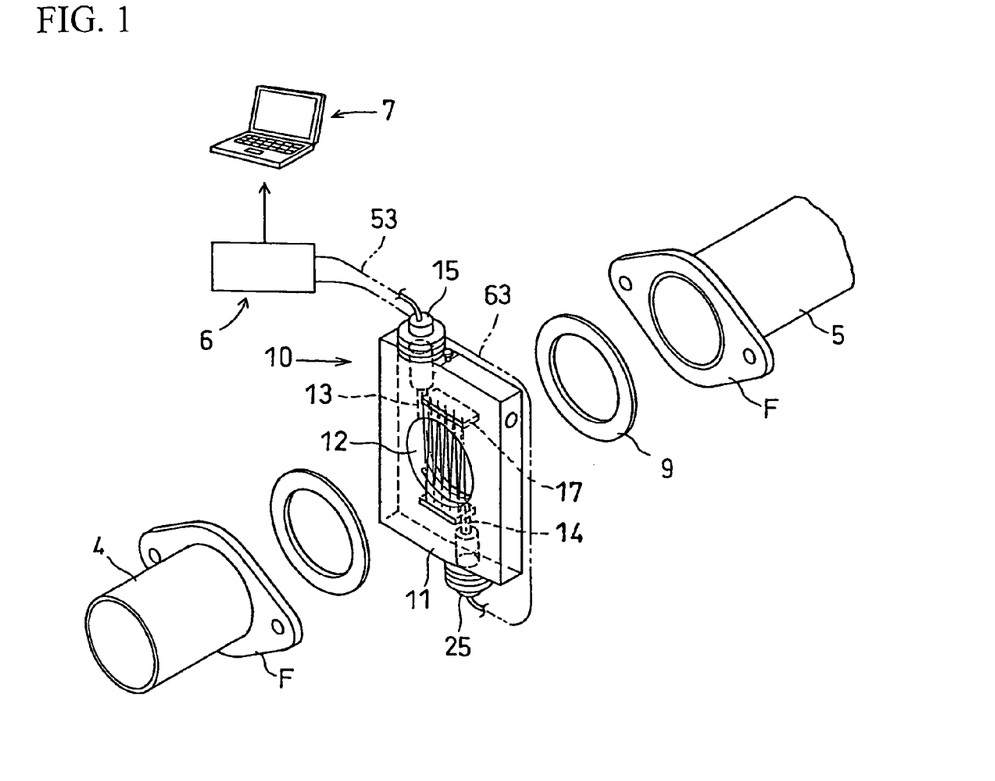
FIG. 1 is an exploded perspective view illustrating the major configuration of a sensor unit in a gas analyzer according to Embodiment 1.
Figure 2:
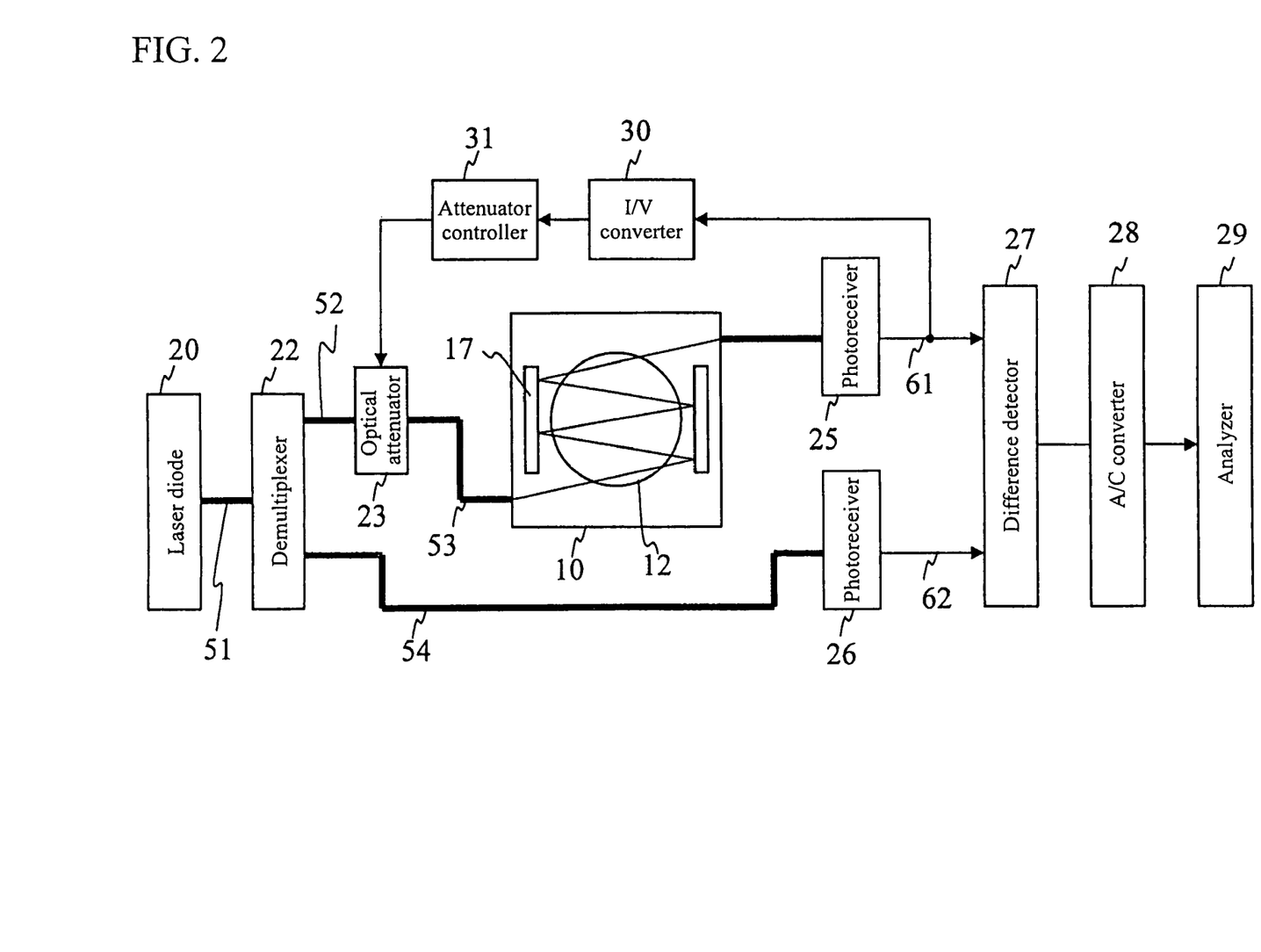
FIG. 2 is a block diagram illustrating a gas analyzer including the major configuration of a laser oscillation/photoreceiving controller and a signal analyzer according to one embodiment.

The following describes a gas analyzing method and a gas analyzer according to the present invention in details, with reference to the drawings. FIG. 1 is an exploded perspective view illustrating the major configuration of a sensor unit in a gas analyzer according to the present embodiment, and FIG. 2 is a block diagram illustrating the overall configuration of the gas analyzer including the major configuration of a laser oscillation/photoreceiving controller and a personal computer as a signal analyzer.

The gas analyzer according to the present invention includes: a sensor unit 10 installed in an exhaust path between exhaust tubes 4, 5 connected with an engine; a laser oscillation/photoreceiving controller 6 that emits laser light applied to exhaust gas and receives an electric signal from a photoreceiver receiving the laser light; and an analyzer 7 including a personal computer that analyzes a component contained in exhaust gas and a concentration thereof based on the light intensity of the received laser light that has passed through the exhaust gas and the light intensity of the laser light that does not pass through the exhaust gas.

The sensor unit 10, as shown in FIG. 1, includes a sensor base 11 made of a plate member with a thickness of about 5 to 20 mm, for example, at a center portion which a through hole 12 is formed with a diameter substantially the same as an inner diameter of an exhaust pipe unit. Through the through hole 12, the exhaust gas flowing through the exhaust path passes. The shape of the through hole 12 is preferably a circle with a diameter substantially the same as the inner diameter of the exhaust pipe unit so as not to disturb the exhaust flow. A metal plate member or a ceramic plate member may be used as the plate member, and a material thereof is not limited especially. The sensor base 11 includes two sensor holes 13, 14 penetrating from an outside face to the through hole 12. To the sensor hole 13, a collimator 15 is fixed for collecting laser light to configure an emission unit, and to the collimator 15 an optical fiber 53 is connected, through which the laser light applies. To the sensor hole 14, a photoreceiver (detector) 25 such as a photodiode is fixed to receive the laser light.

To the sensor base 11, upper and lower two reflecting boards 17, 17 are fixed to be opposed to each other to sandwich the through hole 12 therebetween. The two reflecting boards 17, 17 are fixed to be parallel with each other, so that the laser light applied from the optical fiber 53 on the emission side and collected by the collimator 15 is firstly reflected upward by the lower reflecting board 17, and then is reflected downward by the upper reflecting board 17. In this way, the laser light is reflected alternately by the two reflecting boards 17, 17, thus arriving at the photoreceiver 25 on the photoreceiving side. In this way, the configuration is devised so that laser light travels a long distance in the exhaust gas.

Preferably, the reflecting boards 17 are made of a material less prone to degradation by exhaust gas, and are preferably configured so that a thin film of gold or platinum, for example, is formed on a plate member as a base, on which a thin film of $MgF_2$ or $SiO_2$ is formed as a protective layer. The reflecting boards 17 have preferably a high reflectivity so as to reflect laser light effectively. Since the reflecting boards 17 are exposed to exhaust gas during the operation of the engine, to which dirt may be attached, the reflecting boards 17 are preferably cleaned if needed after the sensor base 11 is removed from flange portions F, F.

The sensor base 11 is disposed between the flange portions F, F, and is fixed by bolts and nuts (not illustrated), for example, so that gaskets 9, 9 are sandwiched between the flange portions F, F and the sensor base 11. The gaskets 9 are made of asbestos, for example, each including a through hole with a diameter the same as the inner diameter of the exhaust tube. With this configuration, even when the sensor base 11 is sandwiched between the flange portions F, F for the connection of the exhaust tube, exhaust gas will not leak from the exhaust path, and the length of the exhaust path is not increased so much.

The optical fiber 53 and the photoreceiver 25 are connected with the laser oscillation/photoreceiving controller 6, the optical fiber 53 supplying the laser light to the sensor unit 10 and the photoreceiver 25 receiving the laser light that has passed through the exhaust gas at the sensor unit 10 and outputting an electric signal. Thus, laser light emitted from a laser diode described later included in the laser oscillation/photoreceiving controller 6 is applied via the optical fiber 53 to the through hole 12 through the sensor hole 13 of the sensor base 11, the laser light reflected between the reflecting boards 17, 17 is received by the photoreceiver 25 on the photoreceiving side through the sensor hole 14, and an electric signal output from the photoreceiver 25 is input to the laser oscillation/photoreceiving controller 6 via a cable 63.

The laser oscillation/photoreceiving controller 6 functions to emit laser light, while receiving an electric signal from the photoreceiver receiving the laser light, and to convert a differential signal into a digital signal and output the same to the computer 7 serving as the analyzer 29. The laser oscillation/photoreceiving controller 6 includes, as shown in FIG. 2, a laser diode 20, a demultiplexer 22, an optical attenuator 23, an A/D converter 28, photoreceivers 25, 26, a difference detector 27, an I/V converter 30, and an attenuator controller 31.

Then, the laser light emitted from the laser diode 20 is guided to the demultiplexer 22, and is demultiplexed by the demultiplexer 22 into measurement laser light and reference laser light. The thus demultiplexed measurement laser light is guided to the optical attenuator 23 via an optical fiber 52, is attenuated by the optical attenuator 23, is guided to the emission unit of the sensor unit 10 via the optical fiber 53, and is applied to the through hole 12 through the emission unit. The laser light applied to the through hole 12 passes through the exhaust gas, which is then received by the photoreceiver 25, and is converted into an electric signal.

In the present embodiment, the measurement laser light demultiplexed by the demultiplexer 22 is applied via the optical attenuator 23 as stated above. This optical attenuator 23 functions to adjust a light intensity of the measurement laser light applied to the exhaust gas, and may be embodied in an appropriate manner, for example, by placing a filter capable of changing a transmittance of the laser light in the optical path to change the transmittance light amount, or by placing a mirror in the optical path and altering the reflecting angle of the mirrors to adjust the light intensity. The attenuation rate of the optical attenuator 23 is controlled by the attenuator controller 31.

The attenuator controller 31 functions so that the light intensity of the measurement laser light that has passed through exhaust gas is made equal to the light intensity of the reference laser light, and is configured to receive an electric signal 61 from the photoreceiver 25 subjected to I/V conversion by the I/V converter 30. Since the reference light is free from disturbance factors during from generation to reception of the laser light, the intensity of the reference light will not change as long as the laser output does not change. Therefore, the light intensity of the reference laser light received by the photoreceiver 26 for reference light is constant, and the attenuator controller 31 receives the light intensity of this reference laser light as an input. The attenuator controller 31 outputs a difference between the light intensity of the reference laser light and the light intensity of the measurement laser light as a feed-back correction amount to the optical attenuator 23.

Based on the feed-back correction amount supplied from the attenuator controller 31, the optical attenuator 23 attenuates the measurement laser light so as to make the light intensity of the measurement laser light received by the photoreceiver 25 equal to the light intensity of the reference laser light received by the photoreceiver 26.

This feed-back control allows the measurement laser light received by the photoreceiver 25 to be controlled always at a constant light intensity even when the degree of dirt on the reflecting boards 17 and the state of the particles floating in the exhaust gas change. Thus, since there is no need in the present embodiment to input a light intensity signal of the measurement laser light to the analyzer 29, the data amount to be input to the analyzer can be reduced.

The difference detector 27 calculates a differential signal based on the electric signal 61 of the measurement laser light that has passed through the exhaust gas and an electric signal 62 of the reference laser light, and this differential signal is amplified by a preamplifier (not shown), for example, and is input to the analyzer 29 via the A/D converter 28. The analyzer 29 finds, based on the differential signal from the difference detector 27, an absorption spectrum absorbed by a gas component in the exhaust gas, and analyzes this absorption spectrum to measure a concentration of the component and a temperature of the exhaust gas.

Herein, a gas component concentration C is calculated from the following equation (1):

$$C = -ln(I/I_0)/kL \qquad (1)$$

In the equation (1), I is the transmitted light intensity, $I_0$ is the incident light intensity, k is absorptance, and L is the transmission distance. Thus, the gas component concentration C is calculated based on the ratio of transmitted light intensity (I) to incident light intensity ($I_0$), i.e., based on a signal intensity ($I/I_0$). In the present embodiment, the transmitted light intensity I is output from the photoreceiver 25 receiving the measurement laser light, and the incident light intensity $I_0$ is output from the photoreceiver 26 receiving the reference laser light that does not pass through gas.

The following describes a method for analyzing gas in the thus configured present embodiment. Laser light emitted from the laser diode 20 arrives at the demultiplexer 22 via an optical fiber 51. Reference light obtained by demultiplexing by the demultiplexer 22 serves as the reference laser light via the optical fiber 54, which is then converted into an electric signal by the photoreceiver 26 and is measured as the incident light intensity $I_0$.

Measurement light obtained by the demultiplexing by the demultiplexer 22 serves as the measurement laser light via the optical attenuator 23, is guided to the radiation unit of the sensor unit 10 via the optical fiber 53, and is applied to the through hole 12 through which exhaust gas passes. At this time, since the optical attenuator 23 is feed-back controlled by the attenuator controller 31 so that the light intensity of the measurement laser light that has passed through the exhaust gas is made equal to the light intensity of the reference laser light, the measurement laser light received by the photoreceiver 25 can be controlled always at a constant light intensity even when the degree of dirt on the reflecting boards 17 and the state of the particles floating in the exhaust gas change.

The measurement laser light is reflected repeatedly between the reflecting boards 17, 17, thus arriving at the photoreceiver 25. The measurement laser light that has attenuated while passing through the exhaust gas is received by the photoreceiver 25 as a transmitted light intensity I, which is then converted into an electric signal and is input to the difference detector 27. The repeated reflection of the measurement laser light lengthens the transmission distance in the exhaust gas, thus increasing the transmission distance L in the above-stated expression (1) and causing an increase in the attenuation amount, and therefore accurate measurement of the component concentration of exhaust gas is enabled.

The difference detector 27 calculates a difference between the reference laser light and the measurement laser light, and supplies a differential signal to the analyzer 29. The analyzer 29 finds an absorption spectrum absorbed by the gas component during the passage through the exhaust gas, calculates the ratio ($I/I_0$) between the light intensity of the reference laser light and the light intensity of the measurement laser light at a peak wavelength that has attenuated while passing through the exhaust gas to calculate the gas component concentration contained in the exhaust gas.

In the present embodiment, although the measurement light passes through the optical attenuator, the reference laser light does not pass through an optical attenuator. However, the reference laser light may be controlled to have a predetermined light intensity by an optical attenuator, whereby a load of the processing by the analyzer at a later stage can be lessened.

Figure 3:
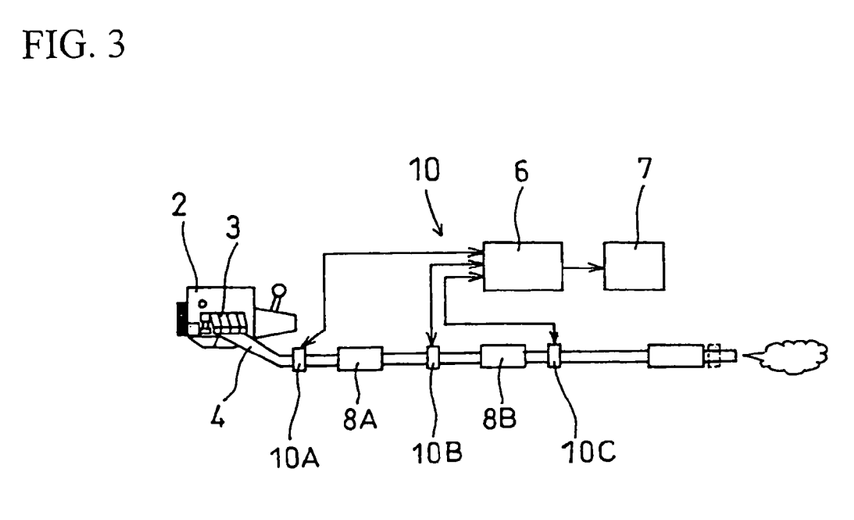
FIG. 3 illustrates the major configuration of an embodiment where a gas analyzer according to Embodiment 2 of the present invention is mounted in an engine bench.
Figure 4:
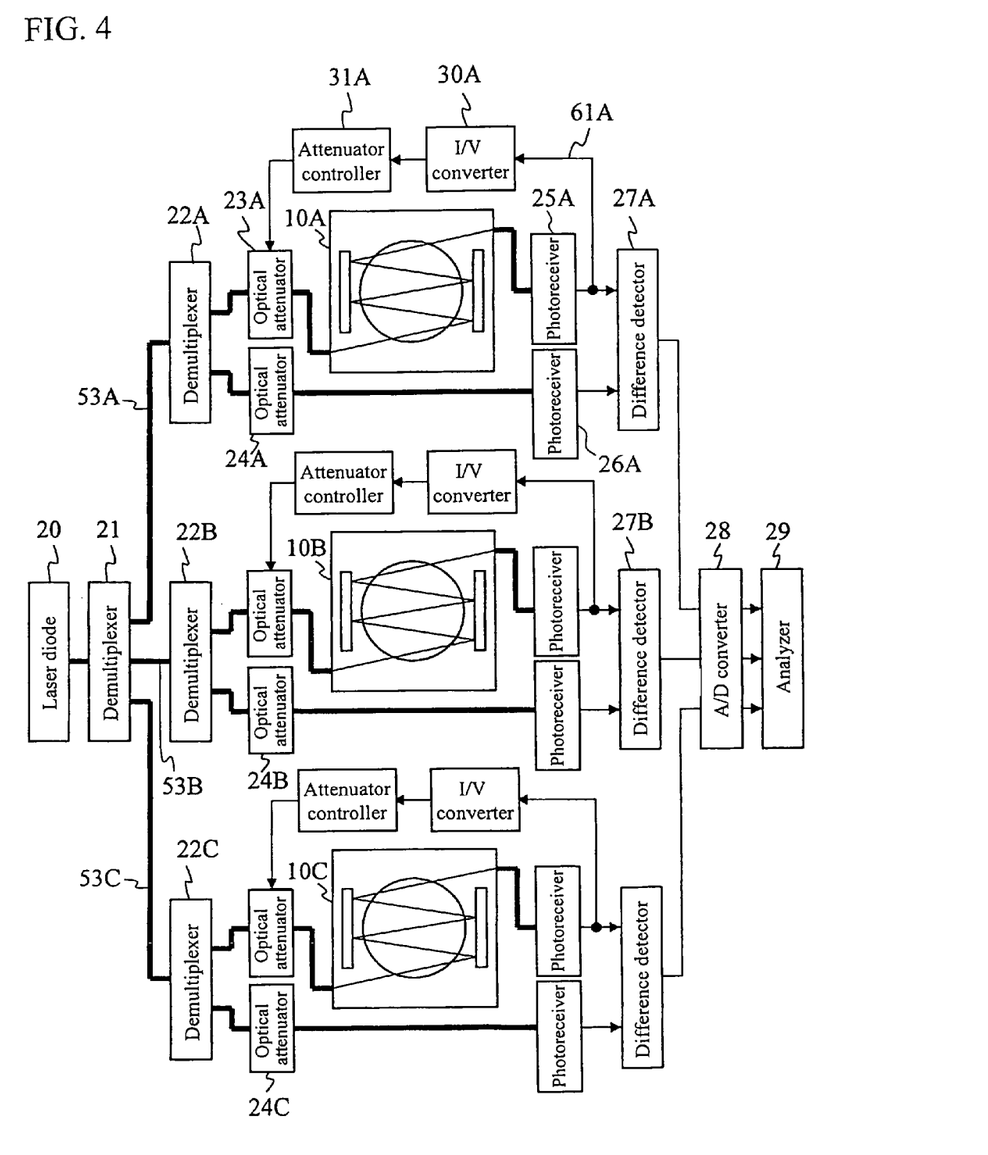
FIG. 4 is a block diagram illustrating a gas analyzer including the major configuration of a laser oscillation/photoreceiving controller and a signal analyzer according to Embodiment 2.

FIGS. 3 and 4 illustrate Embodiment 2 of the present invention, in which FIG. 3 illustrates the major configuration of an embodiment where a gas analyzer is mounted in an engine bench, and FIG. 4 is a block diagram illustrating the overall configuration of the gas analyzer including the major configuration of a laser oscillation/photoreceiving controller and a signal analyzer. In the present embodiment, sensor units are provided at three positions along an exhaust path, and at each of the positions, a gas component contained in exhaust gas and a concentration thereof are analyzed for measurement, and the gas analyzer includes a plurality of sensor units 10A, 10B, and 10C provided at three positions along the exhaust path. The first sensor unit 10A is provided between a first catalyst device 8A and an upstream exhaust tube 4 on an engine 2 side, the second sensor unit 10B is provided downstream of the first catalyst device 8A and the third sensor unit 10C is provided downstream of a second catalyst device 8B.

Then, a demultiplexer 21 functions to demultiplex laser light emitted from a laser diode 20 to be guided to the respective sensor units 10A, 10B and 10C, and the laser light beams demultiplexed by the demultiplexer 21 are guided to demultiplexers 22A, 22B, and 22C via optical fibers 53A, 53B, and 53C, respectively. The laser light beam guided via the optical fiber 53A is demultiplexed by the demultiplexer 22A into measurement light and reference light, and the measurement light passes through an optical attenuator 23A to be measurement laser light, which is then applied to exhaust gas at the sensor unit 10A. The reference light passes through an optical attenuator 24A, and is converted into an electric signal by a photoreceiver 26A. The optical attenuators 24A, 24B, and 24C function so that the reference light at the sensor units 10A, 10B and 10C has a same light intensity, whereby a data amount input to an analyzer 29 can be reduced.

Then, the other configuration is the same as that of the embodiment described with reference to FIGS. 1 and 2.

In the embodiment of FIGS. 3 and 4, the sensor units 10A, 10B and 10C are provided at three positions along the exhaust path, and for each of the positions, a differential signal from a corresponding difference detector 27A, 27B, or 27C is just converted into a digital signal and is sent to the analyzer 29, whereby a gas component contained in the exhaust gas at each of the three positions along the exhaust path and a concentration thereof can be determined. Therefore, the data amount sent from the A/D converter 28 to the analyzer 29 can be controlled within the range of the capacity of a PCI bus in a signal conversion board, while increasing the number of measurement positions.

Figure 5:
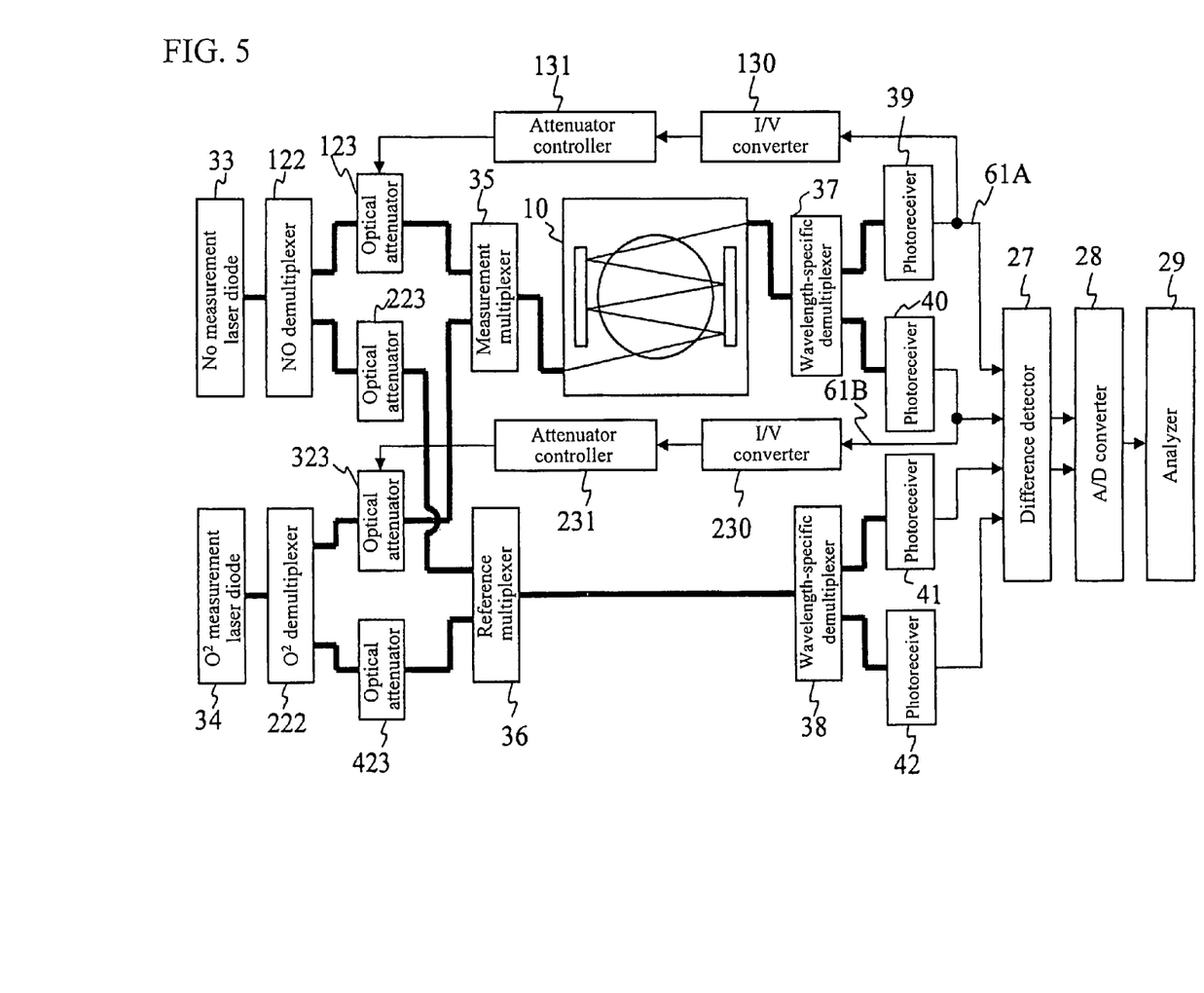
FIG. 5 is a block diagram illustrating a gas analyzer including the major configuration of a laser oscillation/photoreceiving controller and a signal analyzer according to Embodiment 3.

FIG. 5 illustrates a gas analyzer according to Embodiment 3 of the present invention, where a sensor unit is provided at one position of an exhaust path to measure concentrations of NO (nitric monoxide) and oxygen ($O_2$) contained in exhaust gas.

A wavelength of laser light passing through the gas is set in accordance with a gas component to be detected, for example, the wavelength suitable for the detection of oxygen ($O_2$) is 760 nm, the wavelength suitable for the detection of ammonia is 1530 nm, the wavelength suitable for the detection of carbon monoxide is 1560 nm, and the wavelength suitable for the detection of nitric monoxide (NO) is 1796 nm.

Since the wavelength suitable for the detection of oxygen ($O_2$) is far away from the wavelength suitable for the detection of NO, it is impossible for one laser diode to emit light including the both wavelengths.

Thus, a laser oscillation controller 6 includes a NO laser diode 33 that emits laser light to measure the concentration of NO, and an oxygen laser diode 34 that emits laser light to measure the concentration of oxygen, where the NO laser diode 33 and the oxygen laser diode 34 emit the respective laser light in a time-sharing manner.

NO laser light emitted from the NO laser diode 33 is guided to a NO demultiplexer 122 via an optical fiber, and is demultiplexed into NO measurement light and NO reference light. The thus demultiplexed NO measurement light and NO reference light pass through optical attenuators 123 and 223 to be guided to a measurement multiplexer 35 and a reference multiplexer 36, respectively.

Oxygen laser light emitted from the oxygen laser diode 34 is guided to an $O_2$ demultiplexer 222 via an optical fiber, and is demultiplexed into oxygen measurement light and oxygen reference light. The thus demultiplexed oxygen measurement light and oxygen reference light pass through optical attenuators 323 and 423 to be guided to the measurement multiplexer 35 and the reference multiplexer 36, respectively.

The NO measurement light and the oxygen measurement light are multiplexed by the measurement multiplexer 35 to be measurement laser light, which is applied to the exhaust gas through an emission unit of the sensor unit 10, where laser light of a specific wavelength is absorbed by oxygen and NO in the exhaust gas during the passage through the exhaust gas, and the absorbed light is demultiplexed by a wavelength-specific demultiplexer 37 into NO transmitted light and oxygen transmitted light in accordance with the wavelengths. The NO transmitted light is received by a NO photoreceiver 39, is converted into a NO measurement received-light intensity signal 61A as an electric signal, and is transmitted to the difference detector 27 and an I/V converter 130. The oxygen transmitted light is received by an oxygen photoreceiver 40, is converted into an oxygen measurement received-light intensity signal 61B as an electric signal, and is transmitted to the difference detector 27 and an I/V converter 230.

The NO reference light and the oxygen reference light are multiplexed by the reference multiplexer 36 to be reference laser light, which is guided to a wavelength-specific demultiplexer 38 via an optical fiber, and is demultiplexed into NO reference light and oxygen reference light in accordance with the wavelengths. The NO reference light is received by a photoreceiver 41, is converted into an electric signal, and is input to the difference detector 27. The oxygen reference light is received by an oxygen photoreceiver 42, is converted into as an electric signal, and is input to the difference detector 27.

The attenuator controller 131 controls the light intensity of the NO measurement light, and feed-back controls the attenuation ratio of the optical attenuator 123, based on the NO measurement received-light intensity signal 61A I/V converted by the I/V converter 130, so that the light intensity of the NO transmitted light is made equal to the light intensity of the NO reference light.

The attenuator controller 231 controls the light intensity of the oxygen measurement light, and feed-back controls the attenuation ratio of the optical attenuator 323, based on the measurement received-light intensity signal 61B I/V converted by the I/V converter 230, so that the light intensity of the oxygen transmitted light is made equal to the light intensity of the oxygen reference light.

The difference detector 27 finds a difference between the light intensity of the NO transmitted light that has passed through the exhaust gas and the light intensity of the NO reference light that does not pass through the exhaust gas to calculate a NO differential signal. The calculated NO differential signal is converted into a digital signal by an A/D converter 28, and is output to an analyzer (computer) 29. The difference detector 27 finds a difference between the light intensity of the oxygen transmitted light that has passed through the exhaust gas and the light intensity of the oxygen reference light that does not pass through the exhaust gas to calculate an oxygen differential signal. The calculated oxygen differential signal is converted into a digital signal by the A/D converter 28, and is output to the analyzer (computer) 29.

Based on the differential signal between the NO transmitted light and the NO reference light input by the A/D converter 28, the analyzer 29 finds a NO absorption spectrum absorbed by NO in the exhaust gas, and analyzes the NO absorption spectrum to determine a NO concentration. Further, based on the differential signal between the oxygen transmitted light and the oxygen reference light input by the A/D converter 28, the analyzer 29 finds an oxygen absorption spectrum absorbed by oxygen in the exhaust gas, and analyzes the oxygen absorption spectrum to determine an oxygen concentration.

In the present embodiment, the attenuator controller 131 feed-back controls the attenuation ratio of the optical attenuator 123 so that the light intensity of the NO transmitted light is made equal to the light intensity of the NO reference light that is set as a predetermined light intensity. Therefore, the NO transmitted light can be controlled to be always at a predetermined (constant) light intensity, so that the analyzer 29 can find a standardized NO absorption spectrum that can be obtained by emission with the laser light of the predetermined light intensity from the differential signal.

Further, the attenuator controller 231 feed-back controls the attenuation ratio of the optical attenuator 223 so that the optical intensity of the oxygen transmitted light is made equal to the light intensity of the oxygen reference light that is set as a predetermined light intensity. Therefore, the oxygen measurement transmitted light can be controlled to be always at a predetermined (constant) light intensity, so that the analyzer 29 can find a standardized oxygen absorption spectrum that can be obtained by emission with the laser light of the predetermined light intensity from the differential signal.

Thus, since there is no need to input the NO measurement received-light intensity signal 61A and the oxygen measurement received-light intensity signal 61B to the analyzer 29, the data amount transmitted from the A/D converter 28 to the analyzer 29 can be reduced.

In the present embodiment, after letting the laser light pass through the exhaust gas, the measurement laser light obtained by multiplexing the NO measurement light and the oxygen measurement light is demultiplexed into the NO transmitted light and the oxygen transmitted light by the wavelength-specific demultiplexer 37. Further, the reference laser light obtained by multiplexing the NO reference light and the oxygen reference light is demultiplexed into the NO reference light and the oxygen reference light by the wavelength-specific demultiplexer 38. Thus, the feed-back control is enabled so that the light intensity of the NO transmitted light is made equal to the light intensity of the NO reference light.

In the present embodiment, the NO laser diode 33 and the oxygen laser diode 34 emit the respective laser light in a time-sharing manner, and therefore the data amount input to the analyzer 29 can be further reduced. Further, data for the NO measurement is never mixed with data for the oxygen measurement.

Moreover, the oxygen transmitted light and the NO transmitted light are demultiplexed by the wavelength-specific demultiplexers 37 and 38, and are received by the photoreceivers 39, 40, 41, and 42. Therefore, since a photoreceiver that is suitable for a wavelength of laser light to be received can be selected, the photoreceiving accuracy can be enhanced.

In the above description, the NO laser diode 33 and the oxygen laser diode 34 emit the respective laser light in a time-sharing manner. However, these laser diodes may emit laser light constantly.

Figure 6:
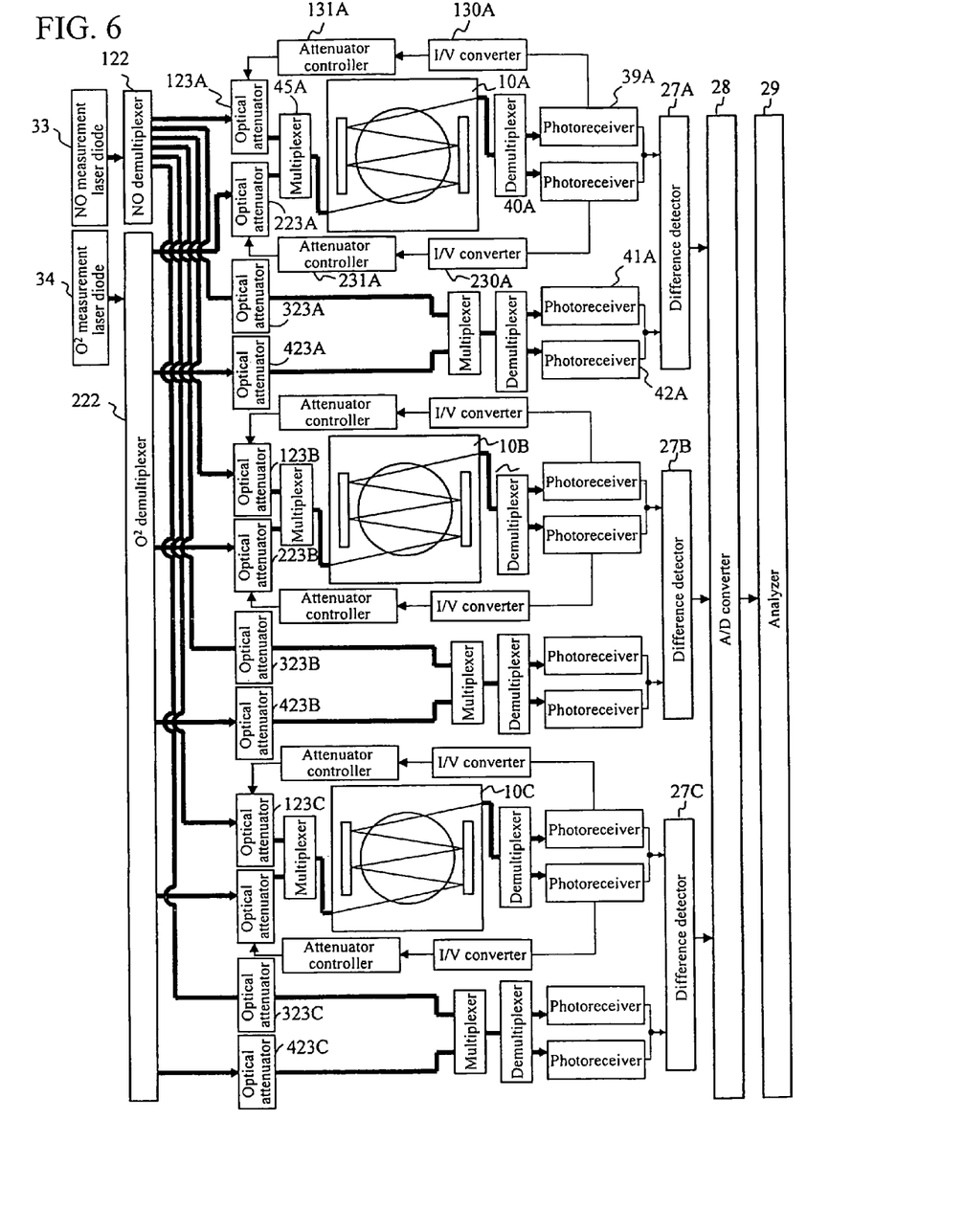
FIG. 6 is a block diagram illustrating a gas analyzer including the major configuration of a laser oscillation/photoreceiving controller and a signal analyzer according to Embodiment 4.

FIG. 6 illustrates a gas analyzer according to Embodiment 4 of the present invention, which is configured so that sensor units 10A, 10B, and 10C are provided at three positions along an exhaust path to measure concentrations of NO (nitric monoxide) and oxygen ($O_2$) contained in exhaust gas.

In the present embodiment, a NO demultiplexer 122 demultiplexes laser light emitted from a NO laser diode 33 into six laser light beams, which are then sent to the respective measurement positions as NO measurement light or NO reference light. Further, an oxygen demultiplexer 222 demultiplexes laser light emitted from an oxygen laser diode 34 into six laser light beams, which are then sent to the respective measurement positions as oxygen measurement light or oxygen reference light. Optical attenuators 323A, 323B, and 323C that attenuate the NO reference light demultiplexed by the NO demultiplexer 122 each has a set attenuation ratio such that their light intensities of the NO reference light can be made equal to each other. Optical attenuators 423A, 423B, and 423C that attenuate the oxygen reference light demultiplexed by the oxygen demultiplexer 222 each has a set attenuation ratio such that their light intensities of the oxygen reference light can be made equal to each other. With this configuration, a load of the processing by the analyzer 29 can be lessened.

In the present embodiment, the sensor units 10A, 10B, and 10C are provided at three positions along an exhaust path to measure concentrations of NO (nitric monoxide) and oxygen ($O_2$) contained in the exhaust gas. Herein, since only three signals are input to the analyzer 29 from difference detectors 27A, 27B and 27C, the measurement positions can be increased within the range of the capacity of a PCI bus in a signal conversion board.

Although that is a detailed description of the embodiments of the present invention, the present invention is not limited to the above-stated embodiments, and the design may be modified variously without departing from the spirits of the present invention defined in the attached claims.

In the above-stated embodiments, the attenuator controller feed-back controls the optical attenuator so that the light intensity of the measurement laser light that has passed through the exhaust gas is made equal to the light intensity of the reference laser light. However, the light intensity of the measurement laser light that has passed through the exhaust gas is not necessarily made equal to the light intensity of the reference laser light. As long as control is conducted by the optical attenuator so that the light intensity of the measurement laser light that has passed through the gas has a predetermined relationship with the light intensity of the reference laser light, the analyzer 29 can make the light intensity of the measurement laser light that has passed through the gas equal to the light intensity of the reference laser light. For instance, when control is conducted so that the light intensity of the measurement laser light that has passed through the gas is P times the light intensity of the reference laser light, then the analyzer 29 multiplies the light intensity of the reference laser light by P times, whereby the light intensity of the measurement laser light that has passed through the gas can be made equal to the light intensity of the reference laser light.

In the above-described embodiments, the gas analyzer of the present invention analyzes a gas component of exhaust gas exhausted from the engine at the sensor unit 10 provided at the exhaust tube of the vehicle. However, the position of the sensor unit provided is not limited to the exhaust tube of the vehicle, and the sensor unit 10 may be provided at any tube through which gas passes, thus enabling analysis of a component of the gas passing therethrough in real time.

INDUSTRIAL APPLICABILITY

According to the present invention, gas is irradiated with measurement laser light via an optical attenuator, and control is conducted by the above-stated optical attenuator so that the light intensity of the measurement laser light that has passed through the gas has a predetermined relationship with the light intensity of the reference laser light. Therefore, there is no need to input data of the light intensity of the measurement laser light that has passed through the gas to an analyzer. Thus, the data amount to be input to the analyzer can be reduced, which is for analyzing a concentration or the like of a gas component contained in the gas based on the measurement laser light that has passed through the gas and the reference laser light that does not pass through the gas. As a result, concentrations of a plurality of types of gas components contained in the gas can be analyzed for measurement at a plurality of positions in real time.

Note that all publication, patent and patent applications mentioned in the present specification are hereby incorporated herein by reference.

The invention claimed is:

1. A gas analyzing method, comprising the steps of:
   demultiplexing laser light by a demultiplexer into measurement laser light and reference laser light; letting the measurement laser light pass through gas to be received by a photoreceiver; finding an absorption spectrum absorbed by a gas component in the gas based on a light intensity of the received measurement laser light and a light intensity of the reference laser light; and analyzing the absorption spectrum to measure a concentration of the gas component,
   wherein the measurement laser light is applied to the gas through an optical attenuator, and control is conducted by the optical attenuator so that the light intensity of the measurement laser light that has actually passed through the gas has a predetermined relationship with the light intensity of the reference laser light,
   wherein a signal of the light intensity of the measurement laser light that has actually passed through the gas is not input to an analysis unit that analyzes the absorption spectrum, so as to reduce an amount of data to be input to the analysis unit.

2. A gas analyzing method, comprising the steps of:
demultiplexing laser light by a demultiplexer into measurement laser light and reference laser light; letting the measurement laser light pass through gas to be received by a photoreceiver; finding an absorption spectrum absorbed by a gas component in the gas based on a light intensity of the received measurement laser light and a light intensity of the reference laser light; and analyzing the absorption spectrum to measure a concentration of the gas component,
wherein the measurement laser light is applied to the gas through an optical attenuator, a signal of the light intensity of the measurement laser light that has actually passed through the gas is fed back to the optical attenuator, and control is conducted by the optical attenuator so that the light intensity of the measurement laser light has a predetermined relationship with the light intensity of the reference laser light,
wherein the signal of the light intensity of the measurement laser light that has actually passed through the gas is not input to an analysis unit that analyzes the absorption spectrum, so as to reduce an amount of data to be input to the analysis unit.

3. The gas analyzing method according to claim 2, wherein the measurement laser light is demultiplexed by a demultiplexer into a plurality of laser light beams, and the demultiplexed plurality of measurement laser light beams are applied to the gas at different positions so as to measure a gas component concentration in the gas at a plurality of positions.

4. The gas analyzing method according to claim 2, wherein the reference laser light is set at a predetermined light intensity by an optical attenuator.

5. A gas analyzing method, comprising the steps of:
demultiplexing a plurality of laser light beams each having a different wavelength band by a demultiplexer into a measurement light beam and a reference light beam; letting the respective measurement light beams pass through optical attenuators and then multiplexing the same to be measurement laser light; letting the measurement laser light pass through gas and demultiplexing the same by a wavelength-specific demultiplexer into transmitted light for each wavelength band; multiplexing the respective reference light beams to be reference laser light and then demultiplexing the same by a wavelength-specific demultiplexer into reference light for each wavelength band; finding an absorption spectrum absorbed by a gas component in the gas based on a light intensity of the transmitted light demultiplexed by the wavelength-specific demultiplexer and a light intensity of the reference light demultiplexed by the wavelength-specific demultiplexer and analyzing the absorption spectrum to measure a concentration of the gas component,
wherein a signal of the light intensity of the transmitted light demultiplexed by the wavelength-specific demultiplexer is fed back to the optical attenuators, and control is conducted by the optical attenuators so that a light intensity of the transmitted light of a certain wavelength band has a predetermined relationship with a light intensity of the reference laser light of the certain wavelength band,
wherein a signal of the light intensity of the measurement laser light that has actually passed through the gas is not input to an analysis unit that analyzes the absorption spectrum, so as to reduce an amount of data to be input to the analysis unit.

6. The gas analyzing method according to claim 5, wherein the plurality of laser light beams each having a different wavelength band are emitted in a time-sharing manner so that each laser light beam is emitted in a different time period.

7. The gas analyzing method according to claim 5, wherein the plurality of laser light beams each having a different wavelength band are emitted from different laser diodes, and are demultiplexed into the plurality of laser light beams by a demultiplexer, and the multiplexed measurement laser light is applied to the gas at different positions so as to measure a gas component concentration in the gas at a plurality of positions.

8. A gas analyzer, comprising:
a demultiplexer that demultiplexes laser light into measurement laser light and reference laser light, the laser light being emitted from a laser light emission unit;
an emission unit that emits gas with the measurement laser light;
a measurement light photoreceiver that receives the measurement laser light that has passed through the gas; and
a reference light photoreceiver that receives the reference laser light;
wherein an absorption spectrum absorbed by a gas component in the gas is found based on a light intensity of the measurement laser light received by the measurement light photoreceiver and a light intensity of the reference laser light received by the reference light photoreceiver, and the absorption spectrum is analyzed so as to measure a concentration of the gas component,
wherein the measurement laser light is applied by the emission unit through an optical attenuator, a signal of the light intensity of the measurement laser light received by the measurement light photoreceiver is fed back to the optical attenuator, and an attenuation ratio of the optical attenuator is controlled so that the light intensity of the transmitted light has a predetermined relationship with the light intensity of the reference laser received by the reference light photoreceiver,
wherein the signal of the light intensity of the measurement laser light that has actually passed through the gas is not input to an analysis unit that analyzes the absorption spectrum, so as to reduce an amount of data to be input to the analysis unit.

9. The gas analyzer according to claim 8, wherein the measurement laser light is demultiplexed by a demultiplexer into a plurality of laser light beams, and the demultiplexed plurality of measurement laser light beams are applied to the gas at different positions so as to measure a gas component concentration in the gas at a plurality of positions.

10. The gas analyzer according to claim 8, wherein the reference laser light is set at a predetermined light intensity by an optical attenuator.

11. A gas analyzer, comprising:
a plurality of laser light emission units that emit a plurality of laser light beams each having a different wavelength band;
a demultiplexer that demultiplexes each laser light beam having a different wavelength band into a measurement light beam and a reference light beam;
a multiplexer that multiplexes the measurement light beams each having a different wavelength band to be measurement laser light;
a multiplexer that multiplexes the reference light beams each having a different wavelength band to be reference laser light;
an emission unit that emits gas with the measurement laser light;

a wavelength-specific demultiplexer that demultiplexes the measurement laser light that has passed through the gas into transmitted light for each wavelength band; and a wavelength-specific demultiplexer that demultiplexes the reference light into reference light for each wavelength band, wherein an absorption spectrum absorbed by a gas component in the gas is found based on a light intensity of the transmitted light demultiplexed by the wavelength-specific demultiplexer and a light intensity of the reference light demultiplexed by the wavelength-specific demultiplexer, and the absorption spectrum is analyzed to measure a concentration of the gas component, wherein the respective measurement light beams are multiplexed by the multiplexer via an optical attenuator, a signal of the light intensity of the transmitted light demultiplexed by the wavelength-specific demultiplexer is fed back to the optical attenuator, and an attenuation ratio of the optical attenuator is controlled so that a light intensity of the transmitted light of a certain wavelength band has a predetermined relationship with a light intensity of the reference light of the certain wavelength band, wherein a signal of the light intensity of the measurement laser light that has actually passed through the gas is not input to an analysis unit that analyzes the absorption spectrum, so as to reduce an amount of data to be input to the analysis unit.

12. The gas analyzer according to claim 11, wherein the plurality of laser light emission units that emit the plurality of laser light beams each having a different wavelength band are emitted in a time-sharing manner so that each laser light beam is emitted in a different time period.

13. The gas analyzer according to claim 11, wherein the laser light beams each having a different wavelength band are emitted from the plurality of laser light emission units, and are demultiplexed into the plurality of laser light beams by a demultiplexer, and the plurality of measurement laser light beams are applied to the gas at different positions so as to measure a gas component concentration in the gas at a plurality of positions.

14. The gas analyzing method according to claim 1, wherein an attenuator controller that controls the optical attenuator receives the light intensity of the reference laser light as an input.

15. The gas analyzer according to claim 8, wherein an attenuator controller that controls the optical attenuator receives the light intensity of the reference laser light as an input.

* * * * *